(12) United States Patent
Ruppert et al.

(10) Patent No.: US 10,463,456 B2
(45) Date of Patent: Nov. 5, 2019

(54) PRODUCTION OF A DENTAL PROSTHESIS BY PRINTING PROSTHETIC BASE ONTO PROSTHETIC TEETH

(71) Applicant: Kulzer GmbH, Hanau (DE)

(72) Inventors: Klaus Ruppert, Maintal (DE); Stefan Brill, Gelnhausen (DE)

(73) Assignee: Kulzer GmbH, Hanau (DE)

( * ) Notice: Subject to any disclaimer, the term of this patent is extended or adjusted under 35 U.S.C. 154(b) by 292 days.

(21) Appl. No.: 15/527,019

(22) PCT Filed: Nov. 23, 2015

(86) PCT No.: PCT/EP2015/077348
§ 371 (c)(1),
(2) Date: May 16, 2017

(87) PCT Pub. No.: WO2016/083296
PCT Pub. Date: Jun. 2, 2016

(65) Prior Publication Data
US 2019/0090995 A1 Mar. 28, 2019

(30) Foreign Application Priority Data
Nov. 25, 2014 (DE) .................. 10 2014 117 222

(51) Int. Cl.
*A61C 13/00* (2006.01)
*B29C 64/10* (2017.01)
(Continued)

(52) U.S. Cl.
CPC ...... *A61C 13/0019* (2013.01); *A61C 13/0004* (2013.01); *A61C 13/0006* (2013.01);
(Continued)

(58) Field of Classification Search
CPC ............ A61C 13/0013; A61C 13/0019; B29L 2031/7536
See application file for complete search history.

(56) References Cited

U.S. PATENT DOCUMENTS 6,497,574 B1 * 12/2002 Miller ............... A61C 7/00
433/213
7,481,647 B2 * 1/2009 Sambu ............. A61C 13/0013
425/436 R
(Continued)

FOREIGN PATENT DOCUMENTS

| CA | 2375889 A1 | 9/2002 |
| CA | 2867771 A1 | 10/2013 |

(Continued)

OTHER PUBLICATIONS

Search Report in International Application No. PCT/EP2015/077348 dated Feb. 3, 2016, 10 pages.
(Continued)

*Primary Examiner* — Benjamin A Schiffman
(74) *Attorney, Agent, or Firm* — Marshall, Gerstein & Borun LLP

(57) ABSTRACT

The invention relates to a method for producing a dental prosthesis, wherein the dental prosthesis comprises a prosthetic base and a plurality of prosthetic teeth, wherein the method is carried out with the use of a virtual three-dimensional dental prosthesis model of the dental prosthesis which is to be produced, and wherein the virtual three-dimensional dental prosthesis model comprises virtual prosthetic teeth and a virtual prosthetic base, including the following chronological steps:

A) producing a physical occlusion plate, wherein a region of the surface of the occlusion plate is formed by a negative of the coronal sides of the virtual prosthetic teeth of the virtual dental prosthesis model, wherein the
(Continued)

location and orientation of the virtual prosthetic teeth relative to one another corresponding to the virtual dental prosthesis model remain retained in the shape of the surface of the occlusion plate;

B) placing and securing preassembled prosthetic teeth on the occlusion plate, wherein the coronal sides of the pre-assembled prosthetic teeth are placed on the surface of the occlusion plate formed by the negative;

C) securing the occlusion plate, with the prosthetic teeth secured therein, in a device for the layered forming of three-dimensional plastic structures; and D) printing the prosthetic base onto the basal ends of the prosthetic teeth with the device for the layered forming of three-dimensional plastic structures on the basis of the shape of the virtual prosthetic base.

The invention also relates to a dental prosthesis produced with such a method and a device for carrying out such a method.

31 Claims, 8 Drawing Sheets

(51) Int. Cl.
| | |
|---|---|
| *B33Y 10/00* | (2015.01) |
| *B33Y 30/00* | (2015.01) |
| *B33Y 80/00* | (2015.01) |
| *B29C 64/124* | (2017.01) |
| *B29C 64/20* | (2017.01) |
| *A61C 13/10* | (2006.01) |
| *A61C 13/36* | (2006.01) |
| *A61C 13/01* | (2006.01) |
| *A61C 13/34* | (2006.01) |
| *A61C 17/00* | (2006.01) |
| *A61C 13/15* | (2006.01) |
| *B29L 31/00* | (2006.01) |

(52) U.S. Cl.
CPC ...... *A61C 13/0013* (2013.01); *A61C 13/0015* (2013.01); *A61C 13/01* (2013.01); *A61C 13/10* (2013.01); *A61C 13/1003* (2013.01); *A61C 13/1016* (2013.01); *A61C 13/34* (2013.01); *A61C 17/036* (2013.01); *A61C 19/003* (2013.01); *B29C 64/10* (2017.08); *B29C 64/124* (2017.08); *B29C 64/20* (2017.08); *B33Y 10/00* (2014.12); *B33Y 30/00* (2014.12); *B29L 2031/7536* (2013.01); *B33Y 80/00* (2014.12)

(56) References Cited

U.S. PATENT DOCUMENTS

| | | | |
|---|---|---|---|
| 9,161,826 B2* | 10/2015 | Ruppert | A61C 13/0013 |
| 9,295,534 B2* | 3/2016 | Ruppert | A61C 13/10 |
| 9,675,435 B2* | 6/2017 | Karazivan | A61C 19/003 |
| 10,299,896 B2* | 5/2019 | Sun | A61C 13/0013 |
| 10,357,344 B2* | 7/2019 | Fisker | B33Y 10/00 |
| 2002/0127345 A1 | 9/2002 | Rheinberger et al. | |
| 2004/0219490 A1 | 11/2004 | Gartner et al. | |
| 2007/0243500 A1 | 10/2007 | Stange et al. | |
| 2012/0258430 A1 | 10/2012 | Ruppert et al. | |
| 2013/0326878 A1 | 12/2013 | Boehm et al. | |
| 2014/0087327 A1 | 3/2014 | Noack | |
| 2014/0131908 A1 | 5/2014 | Sun et al. | |
| 2015/0066181 A1 | 3/2015 | Beyer et al. | |
| 2017/0304033 A1* | 10/2017 | Ruppert | A61C 13/0022 |
| 2018/0344438 A1* | 12/2018 | Boehm | A61C 13/0004 |
| 2019/0090995 A1* | 3/2019 | Ruppert | A61C 13/0004 |
| 2019/0167394 A1* | 6/2019 | Jakson | A61C 13/0019 |

FOREIGN PATENT DOCUMENTS

| | | |
|---|---|---|
| CN | 103237519 A | 8/2013 |
| DE | 3910393 A1 | 10/1990 |
| DE | 4025728 A1 | 2/1992 |
| DE | 10304757 B4 | 8/2004 |
| DE | 10200601765 A1 | 10/2007 |
| DE | 102009056752 A1 | 6/2011 |
| DE | 102012007706 A1 | 10/2013 |
| DE | 102012011371 A1 | 12/2013 |
| EP | 2666438 | 11/2013 |
| JP | 2002284617 A | 10/2002 |
| WO | WO-91/07141 A1 | 5/1991 |
| WO | WO-2011/034781 A2 | 3/2011 |
| WO | WO-2012/155161 A1 | 11/2012 |
| WO | WO-2013/0124452 A1 | 8/2013 |
| WO | WO-2013/156572 A1 | 10/2013 |

OTHER PUBLICATIONS

Office Action in German Application No. 10 2014 117 222.1 dated Aug. 7, 2015, 7 pages.
Office Action in CN Application No. 201580063732.8 dated Jun. 6, 2018, 9 pages.
Office Action in Japanese Application No. 2017-528143 dated Apr. 23, 2018, 2 pages.
International Preliminary Report on Patentability and Written Opinion in International Application No. PCT/EP2015/077348 dated May 30, 2017, 7 pages.

\* cited by examiner

PRODUCTION OF A DENTAL PROSTHESIS BY PRINTING PROSTHETIC BASE ONTO PROSTHETIC TEETH

BACKGROUND OF THE INVENTION

Field of the Invention

The invention relates to a method for producing a dental prosthesis, wherein the dental prosthesis comprises a prosthetic base and a plurality of prosthetic teeth, and wherein the method is carried out by making use of a virtual three-dimensional dental prosthesis model of the dental prosthesis which is to be produced. The invention also relates to a dental prosthesis produced by such a method, a device or combination of devices for carrying out such a method, and an occlusion plate produced by a CAD/CAM process for the implementation of such a method. The conventional method is the analog production of dental prostheses. For the production of the prosthetic base, in most cases an analog method is used at the present time, in which first an impression is taken of the toothless jaw of the patient. From this impression of the toothless jaw, a plaster model of the patient's situation is prepared. Following this, a function model of the prosthesis made of wax is formed on the plaster model and then fitted with prosthetic teeth. Next, a hollow mold or plaster mold of both these parts is prepared, in which the prosthetic teeth are already integrated. As a result the prosthetic teeth are already inserted in the mold. The mold is then poured out with a gum-colored plastic, and, during the casting process, the prosthetic teeth are bonded to the prosthetic base. After the curing of the plastic, the unit undergoes finishing work to obtain the desired shape.

Related Technology

For the production of the dental prosthesis, prosthetic teeth are placed manually and individually on a wax base on a plaster model of the toothless jaw. In the next step, this wax prosthesis is embedded in a flask with plaster, silicone, or gel (depending on the later processing technique), in order then, after the hardening of the embedding material, for the wax base to be washed out with hot water and a hollow cavity created for the prosthesis plastic. The prosthetic teeth remain in this situation in the embedding material. A corresponding plastic is injected or poured into the cavity, resulting in the obtaining of the dental prostheses after the curing of the plastic. During the placement of the preassembled teeth they are adjusted to the respective individual mouth situation of the patient and ground to shape by the dental technician and, if necessary, also by the dentist.

As well as skilled manual techniques, digital manufacturing methods are constantly gaining in importance in the dental sector. Dental prostheses, such as crowns and bridges, have for some years been produced by means of CAD/CAM technologies using milling methods (CAM—Computer-Aided Manufacturing, CAD—Computer-Aided Design).

A CAD/CAM method for producing a dental prosthesis is known from WO 91/07141 A1, wherein, with this method, a prosthetic base formed on the basis of an impression mold is milled out of a plastic block.

Furthermore, generative CAM methods such as SLM (Selective Laser Melting) are increasingly growing in importance for the production of crowns, bridges, and models, as well as stereolithography and DLP (Digital Light Processing) for dental products on a polymer base, such as temporary treatment elements, prostheses, orthodontic and gnatho-orthopaedic apparatus, occlusal splints, drill templates, or dental models. In this situation, the production of prostheses on an acrylate basis by means of RP (Rapid Prototyping) methods has hitherto been subjected to increasingly stringent restrictions. Multi-colored prostheses or prostheses made of different polymer materials (such as for hot-melt compounds and dentine compounds) for producing high-quality and aesthetic prostheses have hitherto only been capable of production by means of elaborate and expensive RP machines with multiple material chambers or by means of elaborate and expensive adhesive bonding and joining techniques.

Likewise, the production of material combinations (such as CoCr and polymer) by means of RP methods has hitherto been very complex and expensive to implement, and not sufficiently developed for series manufacture. The generative production of aesthetically demanding preassembled teeth for part prostheses or total prostheses is not possible at the present time, since only one material or one color can be printed by means of stereolithography. The printing of multicolored preassembled teeth is not possible at the present time. For this reason, the prosthetic base is produced by means of CAM methods (milling or pressing) and preassembled prosthetic teeth are adhesively bonded to the prosthetic base.

DE 10 2012 007 706 A1 discloses the use of a negative mold for the fixing of prosthetic teeth. DE 10 2006 017 651 A1 discloses a forming of a dental prosthesis on a model of a patient's jaw. There are already initial methods known, such as from DE 10 2009 056 752 A1 or WO 2013 124 452 A1, with which a dental part prosthesis or total prosthesis is set up digitally and produced by means of CAD/CAM processes. From DE 103 04 757 B4, a method for producing a dental prosthesis is known with which a virtual setting of the teeth into a virtual model takes place, and the production of a prosthetic base on the basis of the virtual model.

Such methods have the disadvantage that the prosthetic teeth must undergo occlusal adjustment or be removed, wherein the prosthetic base is then ground, or the prosthetic teeth are ground basally in order to adjust their position and location. In most cases, the preassembled prosthetic teeth which produce the best aesthetic results are basally shortened before the bonding, in order to adjust the height of the bite (the occlusion) of the dental prosthesis, resulting in the necessity of providing a rational and economical method for achieving this.

From EP 2 571 451 B1 and EP 2 666 438 A2 methods are known with which prosthetic teeth in a holder are embedded into a wax and then milled basally. The milled teeth are freed from the wax and then inserted into a prosthetic base and adhesively bonded there in order to produce a dental prosthesis.

These methods have the disadvantage that the prosthetic teeth must be inserted individually or in groups into the prosthetic base and adhesively bonded. The correct location for the insertion of the prosthetic teeth into the prosthetic base must, if necessary, in this situation be determined by trial and error. The adhesive bonding of the prosthetic teeth in the prosthetic base incurs a substantial amount of work. In addition to this, the methods are in most cases carried out in such a way that the adhesive or the bonding means emerges from the receiving surfaces between the prosthetic teeth and the prosthetic base, and must then be removed again in order to prevent an aesthetic impairment of the dental prosthesis and to achieve a smooth surface in order to avoid undesirable deposits. During the adhesive bonding, moreover, there is always the possibility of the adhesive agent not applying uniformly or not in a reproducible manner, and thereafter the height of the prosthetic teeth or, respectively, the occlusion of the dental prosthesis is disadvantageously influenced. In extreme cases a coronal subsequent adjustment of the prosthetic teeth must be carried out.

With manual shortening of the preassembled prosthetic teeth, the problem also arises that the basal side (the cervical region) of the prosthetic teeth to be produced exhibits an individual geometry, and before the milling or pressing of the prosthetic base this geometry must be scanned in accordingly and the matching counter-piece for the base plate must be constructed. This too incurs additional effort and expenditure.

SUMMARY

The object of the invention is therefore to obviate the disadvantages of the prior art. In particular, a method is to be provided with which a simple and rapid production of the dental prosthesis can be carried out reproducibly and in high quality. If possible, the adhesive bonding of the prosthetic teeth in the prosthetic base should be avoided. In addition, it should be possible for modern computer-controlled to be used, and for existing data and techniques to be used as far as possible. As well as this, the simplest possible complete and economical processing of the preassembled prosthetic teeth and therefore of the dental prosthesis should be possible.

The object of the invention is solved by a method for producing a dental prosthesis, wherein the dental prosthesis comprises a prosthetic base and a plurality of prosthetic teeth, wherein the method is carried out with the use of a virtual three-dimensional dental prosthesis model of the dental prosthesis which is to be produced, and wherein the virtual three-dimensional dental prosthesis model comprises virtual prosthetic teeth and a virtual prosthetic base, with the following chronological steps:

A) Production of a physical occlusion plate, wherein a region of the surface of the occlusion plate is formed by a negative of the coronal sides of the virtual prosthetic teeth of the virtual dental prosthesis model, wherein the location and orientation of the virtual prosthetic teeth relative to one another corresponding to the virtual dental prosthesis model remain retained in the shape of the surface of the occlusion plate;

B) Placement and securing of preassembled prosthetic teeth on the occlusion plate, wherein the coronal sides of the preassembled prosthetic teeth are placed on the surface of the occlusion plate formed by the negative;

C) Securing of the occlusion plate, with the prosthetic teeth secured therein, in a device for the layered forming of three-dimensional plastic structures; and D) Printing the prosthetic base onto the basal ends of the prosthetic teeth with the device for the layered forming of three-dimensional plastic structures on the basis of the shape of the virtual prosthetic base.

The term "coronal" (Latin corona, 'crown') signifies, at the tooth crown and towards the tooth crown, as a positional and directional designation in relation to the teeth, comprising the occlusal surface and the circumferential regions of the teeth surrounding the occlusal surface. The term "basal" signifies, at the tooth root and towards the tooth root, as a positional and directional designation in relation to the teeth. These terms are also used for prosthetic teeth.

The securing can be particularly preferably provided by means of mechanical tensioning onto the prosthetic teeth. For this purpose the reception surfaces in the occlusion plate can be somewhat smaller, preferably by up to 10% smaller, in relation to the total surface area than the coronal shape of the prosthetic teeth, in order, due to the elastic deformation of the reception surfaces in the occlusion plate, to exert an elastic force onto the prosthetic teeth, which holds the prosthetic teeth in position. As an alternative, adhesive bonding or adherence with wax would also be possible.

As the device for layered forming of three-dimensional plastic structures, use can preferably be made of a 3D printer. Other generative methods, such as, for example, selective laser melting can likewise be used.

With the method according to the invention, it can be provided that, after step B) and before step D), a basal ablation of the preassembled prosthetic teeth secured to the occlusion plate is carried out, wherein the prosthetic teeth are adjusted by the basal ablation to the shape of the virtual prosthetic teeth and/or of the virtual prosthetic base.

The basal ablation of the preassembled prosthetic teeth is carried out according to the invention by milling of the preassembled prosthetic teeth. In this situation, for particular preference, a computer-controlled CAM milling, for example a computer-controlled 4-axle or 5-axle miller, is used.

It is then possible, on the basal side of the prosthetic teeth, which lies opposite the coronal side of the prosthetic teeth, and which, due to the basal ablation of the prosthetic teeth, is adjusted to the planned outer shape of reception surfaces of the virtual prosthetic base, for the prosthetic base to be formed with the device for the layered forming of three-dimensional plastic structures, for example printed on by means of a 3D printer.

With a further development of the present invention, it is proposed that the preassembled prosthetic teeth are basally shortened in such a way that the basal surfaces of all the prosthetic teeth lie in one plane or essentially in one plane.

As a result, a subsequent printing of the prosthetic base onto the basal ends of the prosthetic teeth is facilitated, since the common plane can be particularly easily hardened or cured in a resin bath, or, respectively, the forming with the device for the layered forming of three-dimensional plastic structures, or, respectively, 3D printing can be more easily carried out on a large common surface, and the dental prosthesis obtained is more stable. For this purpose it is important that the virtual models of the prosthetic teeth and/or of the prosthetic base are matched to the outer shape. With the virtual model of the prosthetic teeth and the prosthetic base, a connection surface of the basal end surfaces of the prosthetic teeth is provided for in one plane. If the virtual models of the prosthetic teeth and of the prosthetic base are acquired by file splitting of the dental prosthesis model, the surface of the prosthetic teeth which is intended for the separation is selected such as to correspond to this plane. Laterally, further connection surfaces with the prosthetic base can be provided around the tooth neck of the prosthetic teeth, such that the prosthetic teeth are embedded in the prosthetic base, and not only connected to the prosthetic base via the basal surfaces. Preferably, the basal surfaces of all the prosthetic teeth lie in a plane parallel to the occlusion plate or to the occlusion plane to the transversal plane, related to the patient.

Preferably, the prosthetic base is applied layer by layer onto the prosthetic teeth in such a way that the prosthetic teeth are enclosed not only on the basal underside but also axially round about, such that, for example, interdental spaces can be filled section by section. As a result, the stability of the dental prosthesis is improved.

Provision can further be made for the basally shortened prosthetic teeth to be removed from the occlusion plate and freed of any residues, preferably cleaned of any retaining means for retaining the prosthetic teeth in the occlusion plate, particularly preferably of a wax or a milling wax, wherein the prosthetic teeth are again secured in the occlusion plate before step C).

The wax, milling wax, or the retaining means for connecting the prosthetic teeth to the occlusion plate is in this situation preferably melted out, and the prosthetic teeth are then cleaned of residues with steam or hot water.

As a result it can be ensured that residues which can be present of the retaining means, wax, or milling wax will not impair the printing on of the prosthetic base onto the prosthetic teeth. Otherwise, residues of the retaining means could remain between the prosthetic base and the prosthetic teeth, and thereby mechanically weaken the dental prosthesis at this connection.

With a further development of the method according to the invention, it is also proposed that, for producing the physical occlusion plate, a virtual model of the occlusion plate is calculated from the position and orientation of the coronal sides of the virtual prosthetic teeth of the virtual three-dimensional dental prosthesis model, such that a region of the virtual occlusion plate is formed by a negative of the coronal sides of the virtual prosthetic teeth, wherein the position and orientation of the coronal sides of the virtual prosthetic teeth relative to one another corresponding to the dental prosthesis model remain retained in the negative, and the physical occlusion plate is produced by a CAM process on the basis of the data of the virtual model of the occlusion plate.

As a result, an automation of the production of the occlusion plate, and therefore a further automation of the entire production process can be achieved.

Provision can preferably also be made that, before step C), the prosthetic teeth are basally roughened in at least some regions and/or at least some regions are swelled with a solvent agent, in particular after a cleaning of the prosthetic teeth and after re-securing of the prosthetic teeth in the occlusion plate.

As a result, a more stable connection between the prosthetic teeth and the prosthetic base is achieved. Due to the additional roughing of the surfaces, the solvent can adhere more rapidly to the surfaces. The roughing of the surface can be incurred by the solvent. Moreover, the effective surface for the connection is enlarged by the cement or adhesive, and therefore the retention of the prosthetic teeth in the prosthetic base is improved, and therefore the retention capacity of the dental prosthesis improved. Further, it can be provided that, according to the invention, the prosthetic teeth are cleaned with hot water or steam before the prosthetic base is printed on. Due to the swelling with a solvent, the basal ends of the prosthetic teeth are softened, and can then be more easily mixed with the resin and chemically bonded.

With the preferred methods, provision can also be made that, at the securing of the occlusion plate in the device for the layered forming of three-dimensional plastic structures in step C), the occlusion plate is secured in a holding element on a structuring platform of the device for the layered forming of three-dimensional plastic structures, in a clearly defined position, preferably being latch-fitted into a clearly defined position.

Accordingly, a simple and uncomplicated operation and implementation of the method is achieved. In addition, in this way conventional devices for the layered forming of three-dimensional plastic structures or 3D printers, or devices for the layered forming of three-dimensional plastic structures and 3D printers which are suitable for further or other purposes, are also well-suited for the implementation of the method.

According to the preferred embodiment it is proposed that the printing of the prosthetic base onto the prosthetic teeth takes place in layers.

This layered structure is particularly well-suited for the printing of the prosthetic base onto the prosthetic teeth.

In this situation it can be provided that the printed-on layers of the prosthetic base are applied in a plane parallel to the occlusion plane or to the transversal plane of the denture which is to be produced.

Beginning from the basal side of the aligned prosthetic teeth, if appropriate shortened, roughened, and/or swelled with a solvent, the dental prosthesis can then, without great effort, be prepared in a direction perpendicular to the occlusion plane of the dental prosthesis or perpendicular to the transversal plane of the patient or of the dental prosthesis respectively.

Provision can further be made for the printing to be carried out by the curing of a liquid curable resin on a resin surface of a resin bath, wherein the basal ends of the prosthetic teeth are laid on or at the resin surface and/or the basal ends of the prosthetic teeth are immersed into the resin bath.

In this situation, the basal ends of the prosthetic teeth are laid onto the resin surface both from outside as well as from inside the resin bath, or penetrate through the resin surface. With the layered forming, the prosthetic base can only be aligned with its longitudinal axis parallel to the resin surface if it is intended that a simple performance of the method is to be ensured.

With the use of a resin bath, it can be provided that, according to the invention, for the layered forming, the prosthetic teeth are sunk in the resin bath, wherein an illumination of the liquid resin for the purpose of curing is applied from above the resin surface, or the prosthetic teeth are raised out of the resin bath, wherein an illumination of the liquid resin for the purpose of curing takes place from below the resin surface.

In this context the raising out of the resin bath is favored, since as a result of this it is possible, if appropriate, for work to be carried out without the introduction of additional support structures. Such support structures would otherwise have to be removed with considerable effort after the production of the dental prosthesis.

Further, with forming by raising out of the resin bath, with the forming of the prosthetic base taking place in this case downwards, it is possible for macromechanical retention elements to be introduced on the basal sides of the prosthetic teeth (surface roughing and structures), since with this arrangement the application of the new resin layer will not be smoothed due to wiping.

Furthermore, it can be provided that, according to the invention, after step D), the dental prosthesis, comprising the printed-on prosthetic base and the prosthetic teeth secured therein, is taken out of the occlusion plate, and then a cleaning takes place of the dental prosthesis, a post-curing of the dental prosthesis, and/or a polishing of the prosthetic base.

As a result, a high aesthetic quality and high quality of the product are attained with regard to use as a dental prosthesis. Due to a particularly smooth surface, the dental prosthesis is protected against plaque deposits and acquires a particularly natural appearance.

With the method according to the invention, it can be provided that for the virtual three-dimensional dental prosthesis model is divided computationally by way of file-splitting into a three-dimensional model of the virtual prosthetic teeth and a virtual three-dimensional model of the prosthetic base.

In this situation provision can preferably be made that, at the division of the virtual dental prosthesis model, reception surfaces are calculated into the virtual model of the prosthetic base, in particular reception surfaces calculated such as to be arranged in a plane parallel to the occlusion plate or occlusion plane or to the transversal plane into the virtual model of the prosthetic base, which match the basal sides of the virtual model of the prosthetic teeth, such that the mold of the virtual model of the prosthetic base can be connected flush-surface to the mold of the basal sides of the virtual model of the prosthetic teeth, or they can be laid against one another.

By these means the situation is attained in that the prosthetic base which is printed with the aid of the virtual models onto the prosthetic teeth matches the basal ends of the prosthetic teeth, and can be printed onto the prosthetic teeth in a matched and matching manner and flush-surface, and therefore in a stable manner, and the prosthetic teeth and the prosthetic base can thereby be secured in a more stable manner into one another.

Provision can further be made for the virtual three-dimensional dental prosthesis model to be produced on the basis of an intraoral scan for shaping the virtual prosthetic base and by a virtual setting of virtual models of the preassembled prosthetic teeth in the virtual prosthetic base, wherein preferably the shape, the location, and/or the orientation of the prosthetic teeth are selected by a simulation of the position of the dental prosthesis in the oral cavity of the patient, and wherein for particularly preferably the occlusion plane and/or the chewing movements of the oral cavity are simulated.

As a result, a further automation of the method is achieved. Due to the fact that the virtual model of the dental prosthesis model is used in any event, a virtual model of the occlusion plate can likewise be calculated without very much additional effort. Accordingly, such a production of data is particularly advantageous for this purpose.

Preferred methods can also be characterized in that the preassembled prosthetic teeth can be basally ablated on the basis of the virtual model of the prosthetic teeth with a CAM method, in particular by milling, such that the basal shape of the preassembled prosthetic teeth is adjusted to the virtual prosthetic base in such a way that the outer shape of the prosthetic base fitted corresponds to the outer shape of the virtual dental prosthesis model.

As a result, the basal shortening of the preassembled prosthetic teeth can be achieved with the aid of the virtual model, such that a more complete automation of the method according to the invention is achieved.

Provision can also be made that, for the calculation of the virtual dental prosthesis model, data relating to the outer shape of known preassembled prosthetic teeth is used.

By way of this measure, the scanning in or, respectively, the measuring out of the preassembled prosthetic teeth can be avoided, and thereby further simplification of the method achieved.

Finally, provision can also be made for the preassembled prosthetic teeth fitted to the occlusion plate are fixed to the occlusion plate with the aid of a fluid fixing means which is to be hardened, in particular a wax or resin, in a holding element, and the holding element is then fixed in the device for the layered forming of three-dimensional plastic structures or in a computer-controlled milling device in order to print on the prosthetic base, in order for the prosthetic teeth then to be ablated basally and/or roughed, wherein preferably the basal sides of the preassembled prosthetic teeth project out of the fixing means.

The holding element can be of a simple shape, such as a ring, in which the fixing means is secured in order to fix the preassembled prosthetic teeth and the occlusion plate. The ring requires a marking in order to ensure a clear and unmistakable direction for the position of the prosthetic teeth and/or an unmistakable fixing in the milling machine and/or the device for the layered forming of three-dimensional plastic structures. The marking can, for example, be a groove or a pin. In this situation, a fixing also takes place of the preassembled prosthetic teeth with the occlusion plate. The ablation takes place by milling off the basal sides of the prosthetic teeth. Due to the fixing means, the occlusion plate with the preassembled prosthetic teeth can be fitted in existing conventional molds or holding elements or milling holding elements. Regardless of the shape of the occlusion plate and the prosthetic teeth, these can be connected to the holding element, such that securing is possible in a device for the layered forming of three-dimensional plastic structures, or, respectively, a common processing of the basal sides of the prosthetic teeth.

With these embodiments, it can be provided that the fixing means are removed after the prosthetic teeth have been basally ablated, wherein theoretically the prosthetic teeth can remain secured to the occlusion plate, and wherein preferably the prosthetic teeth are detached from the occlusion plate, and wherein, preferably, the fixing means, the wax, or the resin for removing the fixing means, in particular the wax or resin, are melted and/or washed out.

With the invention it is also proposed that the printing of the prosthetic base onto the basal ends of the prosthetic teeth takes place in layers, wherein the thickness of the layers is always the same.

Due to the application of equal layer thicknesses, the calculation of the data for the production of the prosthetic base in the CAM process is simplified and standardized.

Provision can also be made according to the invention that printing of the prosthetic base onto the basal ends of the prosthetic teeth takes place layer by layer, wherein the thickness of the printed-on plastic structure measures for each layer 1 µm to 500 µm, preferably 10 µm to 200 µm, for particular preference 25 µm to 100 µm.

With the layer thicknesses given, a rapid and precise forming of the prosthetic base can be attained, without this having to undergo wearisome subsequent adjustment.

The objects on which the present invention is based are also solved by a dental prosthesis produced with such a method.

The objects on which the present invention is based are further solved by a device or combination of devices for carrying out the layered forming of three-dimensional plastic structures and a computer for the calculation of the virtual model and to control the CAM device, preferably additionally comprising a computer-controlled milling device.

Finally, the objects on which the present invention is based are also solved by an occlusion plate produced by a CAD/CAM process for implementing such a method.

The prosthetic teeth and/or the prosthetic base preferably consist of a plastic, and for particular preference the prosthetic teeth consist of polymethyl methacrylate (PMMA).

The preassembled prosthetic teeth can be present individually and/or in a plurality of groups or conjoined as complete rows of teeth. Conjoined prosthetic teeth are securely connected to one another.

In the present case, within the framework of the invention, the generally known term Rapid Prototyping method (RP method) is used for a production method with which the occlusion plate is produced with a manufacturing method conventional for rapid prototyping. Since the occlusion plate is not a prototype, but a finished or semi-finished product, it would be possible, instead of the term "Rapid Prototyping method", also in such connections to use occasionally used terms such as "Rapid Manufacturing", "generative manufacturing processes", "Rapid Product Development", "Advanced Digital Manufacturing", or "E-Manufacturing". The prosthetic base is preferably made of a pink-colored artificial resin, and the prosthetic teeth are made of several tooth-colored plastics.

The invention is based on the surprising finding that the prosthetic teeth aligned in relationship to one another corresponding to a three-dimensional model of the dental prosthesis can be used directly as a basis for the printing of the prosthetic base. As a result, it is possible to do away entirely with the use of an adhesive for connecting the prosthetic base to the prosthetic teeth and the process of adhesive bonding. As a result of this, the expense and effort are also avoided of the method steps necessary for these processes, and the risk of possible errors in the adhesive bonding process, which could lead to an impairment in the quality of the dental prosthesis. Since with modern methods the dental prosthesis is in any event generatively prepared, there is only a small amount of extra effort involved in the production of the prosthetic base, which would be required in any event. As a result, with the present invention a method is provided which, with a reduction in the effort and costs, achieves a more stable result with regard to the dental prosthesis. In order to achieve a dental prosthesis which is particularly mechanically stable, it is a practical idea for the prosthetic teeth to be prepared by swelling with a solvent and/or by roughing and/or by cleaning, to achieve a more stable connection to the material of the prosthetic base which will be basally printed onto the prosthetic teeth.

With the present invention, a method is provided with which preassembled prosthetic teeth can be connected to the prosthetic base in one working step, making use of the data from an intraoral scan or scans of the plaster model of a toothless or partially toothed jaw and a virtual setting formation and/or articulation.

BRIEF DESCRIPTION OF THE DRAWINGS

Exemplary embodiments of the invention are explained hereinafter on the basis of eight schematically represented figures, but without the invention being thereby restricted. The figures show.

DETAILED DESCRIPTION

Figure 1:
FIG. 1: a perspective view of a CAD model of a prosthetic base for an upper jaw.

FIG. 1 shows a perspective view of a virtual CAD model of a prosthetic base 1 for carrying out a method according to the invention. Provided in the upper side of the virtual model of the prosthetic base 1 are a plurality of surfaces 2 (reception surfaces 2) for the fixing of prosthetic teeth (not shown in FIG. 1). A physical prosthetic base 1 is produced on the basis of the virtual CAD model, which was produced by means of file-splitting from a virtual dental prosthesis model containing the data relating to the surface of the prosthetic base 1 and of virtual prosthetic teeth, wherein the physical prosthetic base 1 is produced by the printing of the prosthetic base 1 onto the basal ends of the prostheses teeth, aligned on the basis of the dental prosthesis model. To produce the real prosthetic base 1, the virtual CAD model of the prosthetic base 1 is printed out with a 3D printer as the device for the layered forming of three-dimensional plastic structures onto the physical prosthetic teeth. The physical prosthetic base 1 then consist of a pink-colored plastic or, respectively, of a pink-colored light-curable artificial resin. The coloration and transparency are selected such as to match the appearance of a gum. For the sake of simplicity, in the present case no distinction is made with regard to the reference numbers between the physical parts and the virtual models.

The virtual dental prosthesis model is produced by an intraoral scan of the patient or a scan of a plaster model of the oral cavity of the patient first being carried out. Based on this data, a virtual formation arrangement of the prosthetic teeth is prepared, wherein, preferably, account is also taken of the articulation of the jaw of the patient. For this purpose virtual CAD models are used of the preassembled prosthetic teeth which are to be used, which are arranged in a virtual prosthetic base mold.

Figure 2:
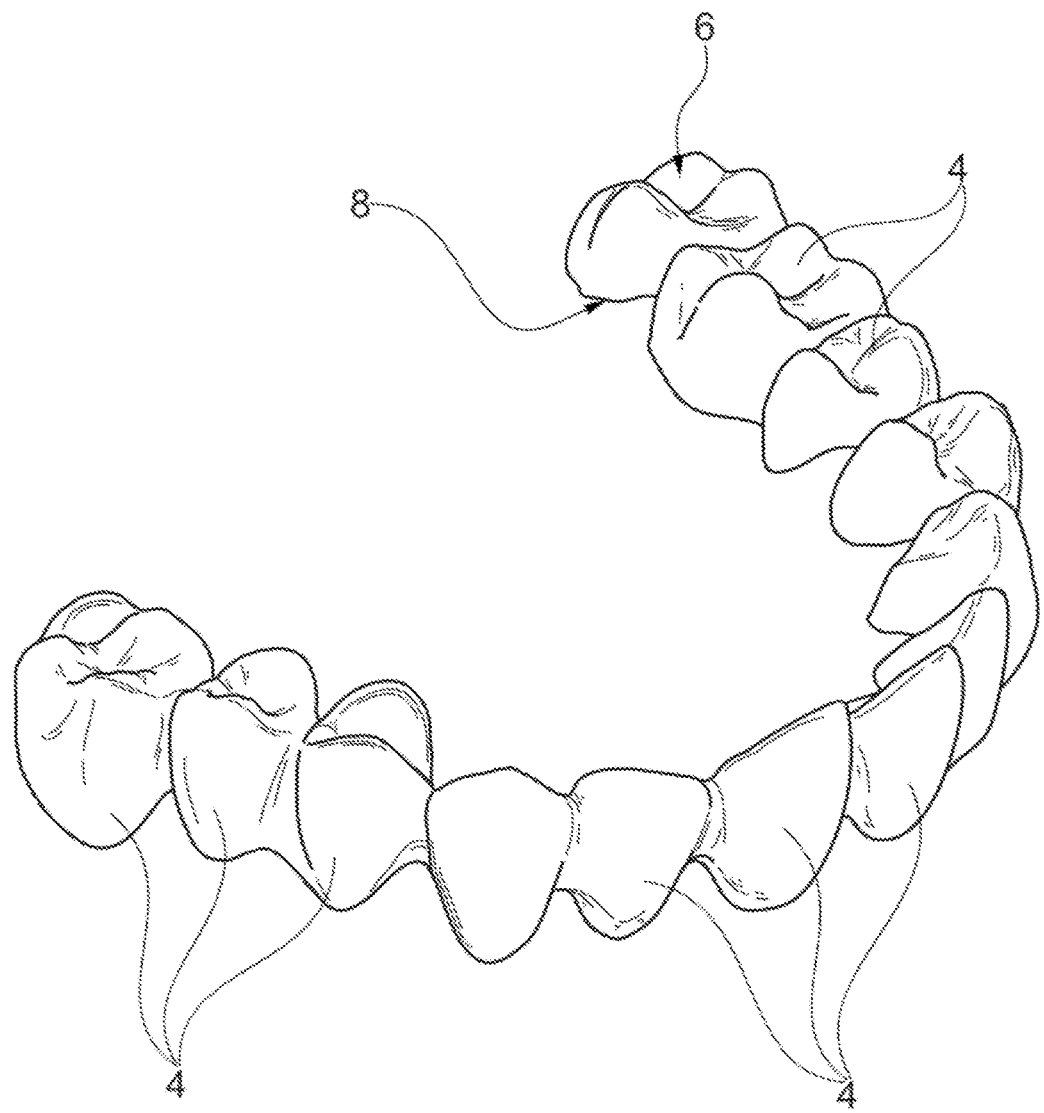
FIG. 2: a perspective view of a virtual CAD model of prosthetic teeth.

FIG. 2 shows a perspective view of a virtual CAD model of the prosthetic teeth 4 which are to be produced or are to be aligned in relation to one another. The mold shown in FIG. 2 corresponds to the portions of the virtual dental prosthesis model left remaining by the file splitting, such that the virtual model of the prosthetic teeth 4 according to FIG. 2 and the virtual model of the prosthetic base 1 according to FIG. 1 when assembled produce the virtual dental prosthesis model.

Attention is drawn to the fact that the real prosthetic teeth 4 are preferably present individually and are not connected to one another, although this is represented as such in FIG. 2. The method according to the invention can also be carried out, however, with teeth rows of prosthetic teeth 4 connected to one another, which are all connected to one another or connected in groups.

The real prosthetic teeth 4 consist of a hard white plastic with a coloration and transparency which matches teeth or matches the teeth of the patient. Each prosthetic teeth 4 comprises a coronal surface 6 (chewing surface) and a basal surface 8. The prosthetic base 1 will later be printed onto the basal surface 8, such that the surfaces 2 for fixing the prosthetic teeth 4 in the prosthetic base 1 lie on the basal surfaces 8 of the prosthetic teeth 4. The surfaces 2 then match the basal counter-pieces on the basal side 8 of the prosthetic teeth 4, since the prosthetic base 1 is printed directly onto the basal surfaces 8 of the prosthetic teeth 4. The basal sides 8 of the prosthetic teeth 4 are produced or processed according to the invention by basal ablating, in particular by grinding or milling, of preassembled prosthetic teeth.

Figure 3:
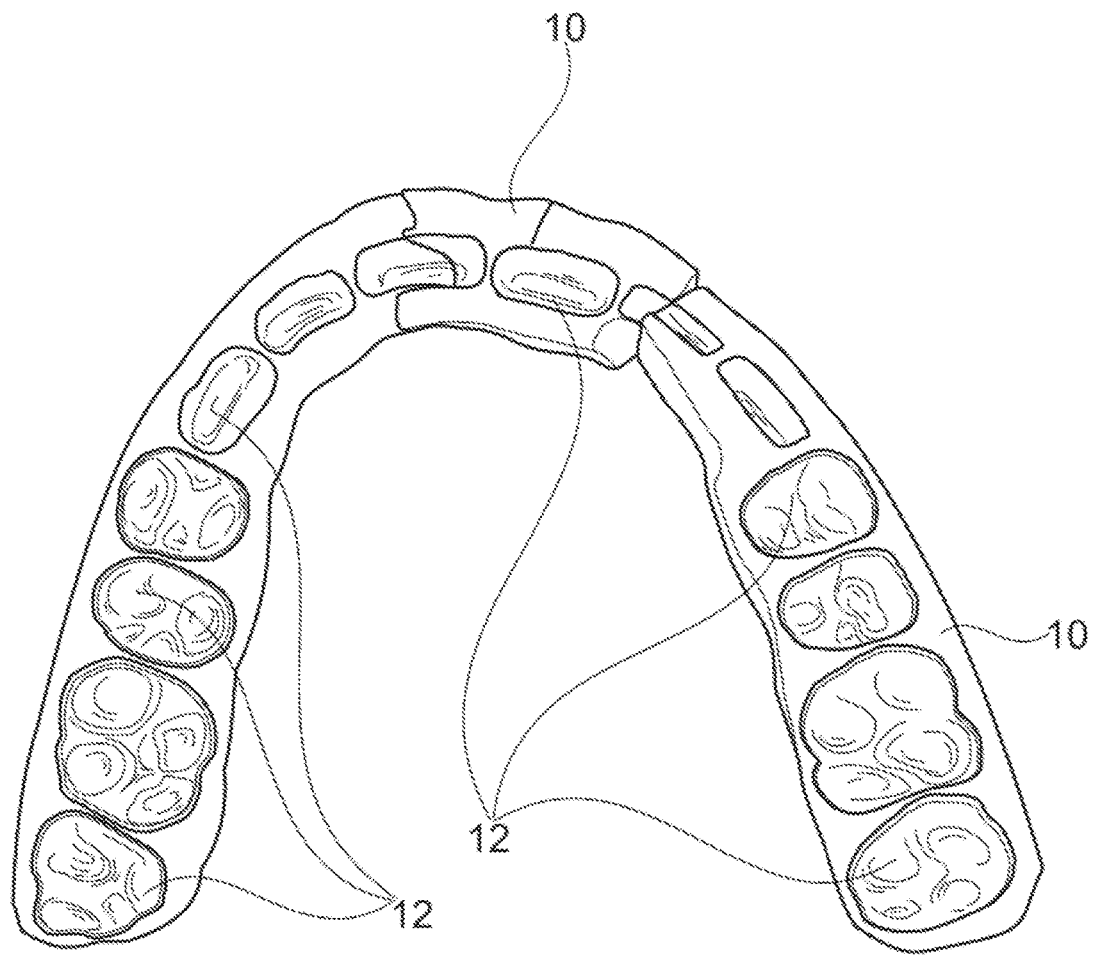
FIG. 3: a view from above onto an occlusion plate for carrying out a variant according to the invention.

For the prosthetic teeth row, a thin plate is now produced with an occlusion relief, referred to as an occlusion plate, by means of CAM processes (milled or pressed), in order for the prosthetic teeth 4 to be easily fixed exactly in this previously determined spatial arrangement. FIG. 3 shows a perspective view from above onto such an occlusion plate 10 for carrying out a method according to the invention. The occlusion plate 10 is produced in that the mold of the surface of all coronal sides 6 of the prosthetic teeth 4, in the orientation and arrangement in relation to one another provided from the virtual dental prosthesis model or the virtual CAD model of the prosthetic teeth 4 according to FIG. 2, is used as a CAD model for a surface of the occlusion plate 10. The other surfaces of the CAD model of the occlusion plate 10 can easily be automatically supplemented, as a dental arch shape with a flat underside and a thickness adjusted to the height of the milling holding element which is to be used later, or in the manner of a bite splint. Optionally, the occlusion plate 10 can also be subdivided into a plurality of segments, which are merged together by means of connection elements in a predefined geometry.

The CAD model of the occlusion plate 10 is used in order to produce the real occlusion plate 10, shown in FIG. 3, from plastic with a CAM method, for example by an RP process. For example, the occlusion plate 10 is produced with the same 3D printer with which the prosthetic base 1 is also printed onto the prosthetic teeth 4. The surface shown in FIG. 3 of the occlusion plate 10 comprises receiver surfaces 12 in the form of depressions, which correspond to the coronal shape of the preassembled prosthetic teeth 4 which are to be processed.

Figure 4:
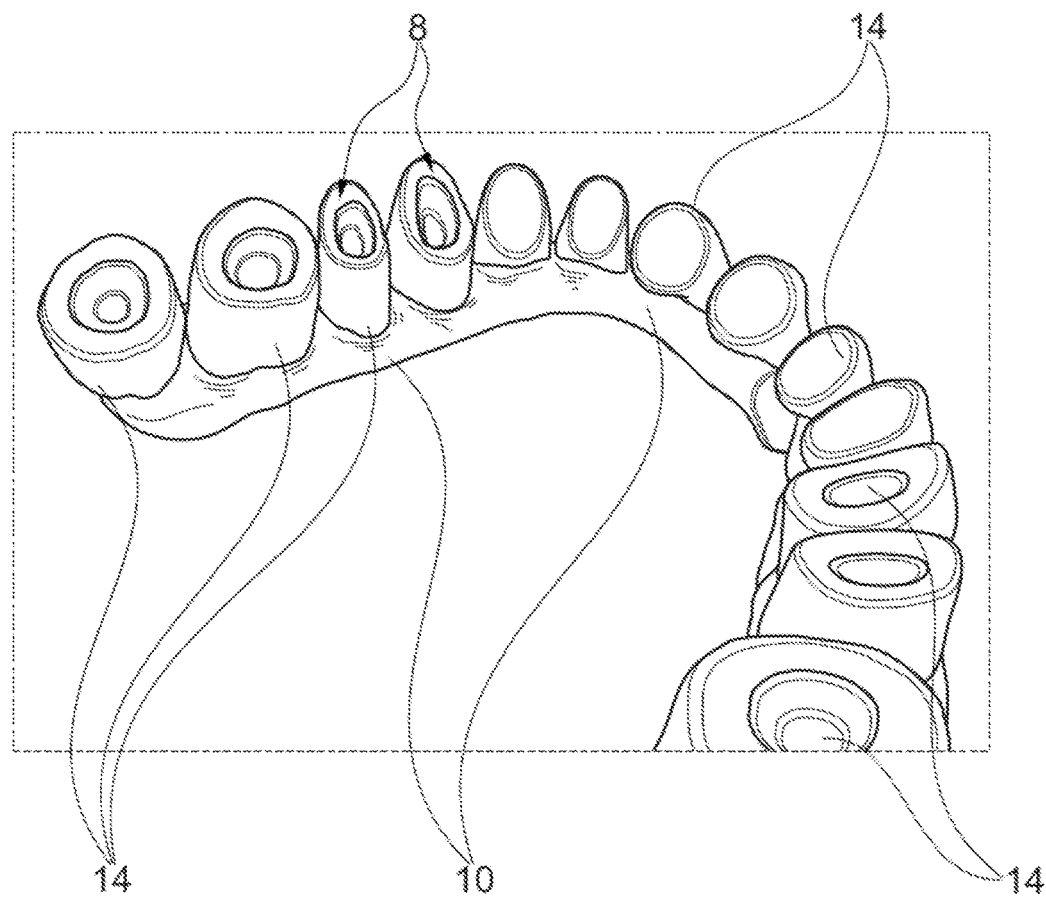
FIG. 4: a perspective part view of the occlusion plate according to FIG. 3 with preassembled prosthetic teeth laid in position/inserted.

FIG. 4 shows a perspective part view of the occlusion plate 10 according to FIG. 3, with prosthetic teeth 14 placed at the receiver surfaces 12 or inserted into the receiver surfaces 12. The preassembled prosthetic teeth 14 are placed with the coronal side on or in the respective matching receiver surfaces 12 of the occlusion plate 10. The basal sides 8 of the preassembled prosthetic teeth 14 are then freely accessible. Ideally and according to the invention, the shape of the receiver surfaces 12 of the occlusion plate 10 is particularly preferably produced in such a way that the inserted preassembled prosthetic teeth 14 are inserted with their coronal sides in a press matching position in the occlusion plate 10. The preassembled prosthetic teeth 14 cannot then spontaneously fall out of the occlusion plate 10 again. As an alternative or in addition, however, it is also possible for an adherence agent to be introduced between the preassembled prosthetic teeth 14 and the receiver surfaces 12, or to be applied on the preassembled prosthetic teeth 14 and/or the receiver surfaces 12. In this working step, the preassembled prosthetic teeth 14 do not yet need to be fixed, even when they are inserted.

Figure 5:
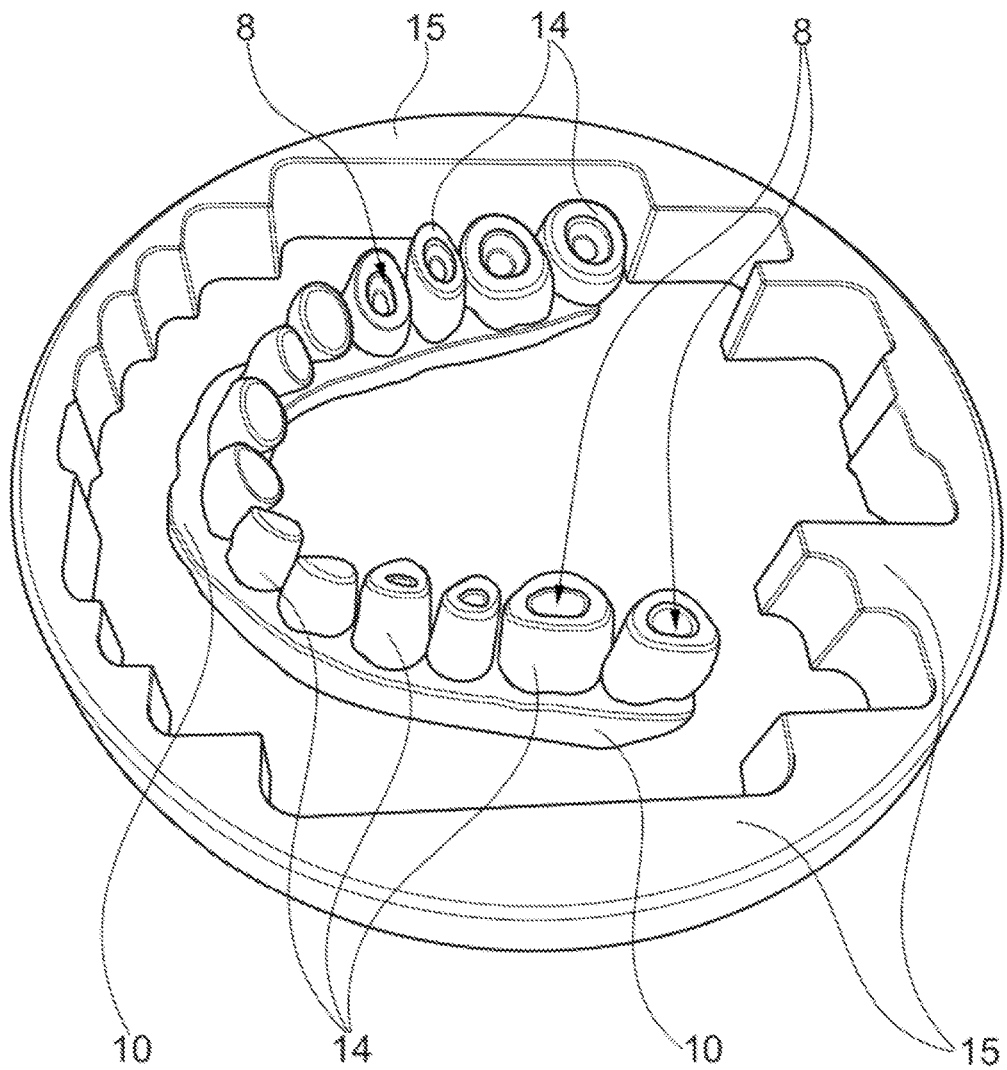
FIG. 5: a perspective view of the occlusion plate according to FIG. 4 fitted with prosthetic teeth, which have been inserted into a milling holding element.

FIG. 5 shows a perspective view of the occlusion plate 10 fitted with the preassembled prosthetic teeth 14, according to FIG. 4, which has been placed in a milling holding element 15. The arrangement of occlusion plate 10 and preassembled prosthetic teeth 14 is therefore set into the milling holding element 15 for a milling machine. In this situation, small cut-out apertures in the milling holding element 15, with corresponding counter-pieces in the occlusion plate 10, help to position the occlusion plate 10 exactly in the milling holding element 15. Such cut-out apertures are not necessary, however; i.e. the inner structure of the milling holding element 15, as shown in FIG. 5, is not necessary for the implementation of the method according to the invention.

This milling holding element 15 is formed by a plastic ring with known external dimensions. In the interior of the ring, in the present case, a profile is provided, which serves for better fixing and orientation of the occlusion plate 10 in the milling holding element 15.

The free space which still exists between the occlusion plate 10, milling holding element 15, and preassembled prosthetic teeth 14, is then cast with a wax 16 or with a milling wax 16 up to the neck region of the prosthetic teeth 14. The wax 16 hardens and fixes the occlusion plate 10 and the preassembled prosthetic teeth 14 in the milling holding element 15. The milling holding element 15 is then clamped into a computer-controlled 4-axis or 5-axis milling machine, and the preassembled prosthetic teeth 14 are then milled down basally, fully automatically, to match with the virtual model shown in FIG. 2 of the prosthetic teeth 4 which are to be shortened. Preferably, in this situation the basal sides 8 of the prosthetic teeth 4 are all shortened in such a way that all the basal surfaces lie in one plane (differently from the representation in FIGS. 5 and 6), and particularly preferably in such a way that all the basal surfaces lie in one plane with a precision of at least 1 mm, and for very particular preference lie in one plane with a precision of at least 0.1 mm. For the milling off, the milling holding element 15 exhibits a marking for the orientation of the occlusion plate 10 and for the insertion into the milling machine, since otherwise an ordering arrangement of the prosthetic teeth 14 in the milling machine is not possible without further action. It can accordingly also be provided that a groove or a blind hole is introduced as a marking on the outer surface, in order to allow for a determination of the location and orientation of the prosthetic teeth 4 in the device for the layered forming of three-dimensional plastic structures or, respectively, in the 3D printer.

Figure 6:
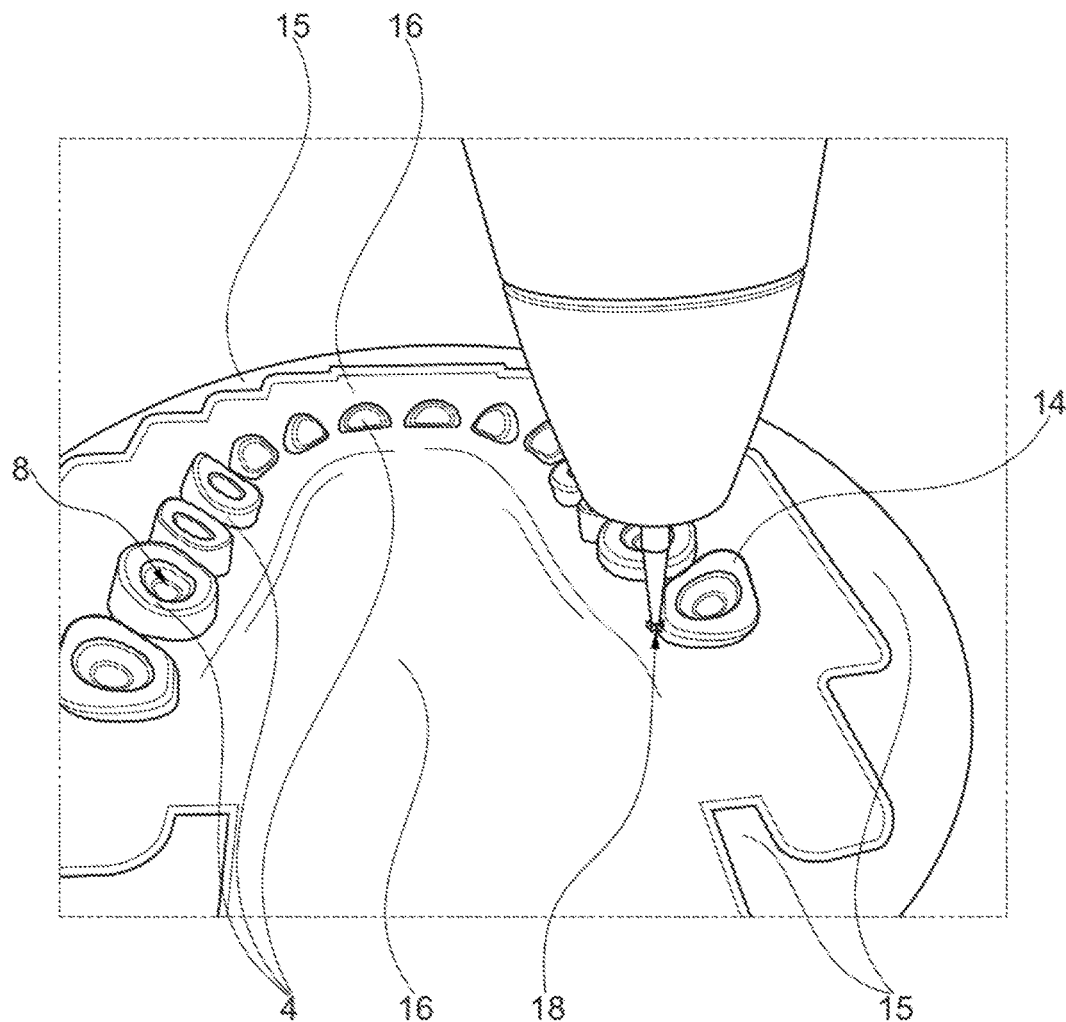
FIG. 6: a perspective view of the occlusion plate, cast in wax or milling wax respectively, connected to the milling holding element and fitted with prosthetic teeth, wherein the prosthetic teeth are basally milled.

This situation is shown in FIG. 6, in which a perspective view is represented of the occlusion plate 10, cast in wax 16, connected to the milling holding element 15, and fitted with prosthetic teeth 4, 14, wherein the preassembled prosthetic teeth 14 have already been basally milled or the prosthetic teeth 4 have already been basally milled off. Once the prosthetic teeth 4 have been produced with the desired shape from the preassembled prosthetic teeth 14, the prosthetic base 1 can be printed onto the prosthetic teeth 4 for the formation of a dental prosthesis. Preferably, however, first the ground prosthetic teeth 4 are freed from the wax 16, released from the holding element 15 and from the occlusion plate 10, and then cleaned, in order to release any residues from the surfaces of the prosthetic teeth 4. The removal of wax residues can be carried out, for example, by washing with hot water or steam. As an alternative, the prosthetic teeth 4 can in this situation remain in the occlusion plate 10. The cleaned prosthetic teeth 4 are then again inserted into the occlusion plate 10 and secured in a holding element of a 3D printer.

Figure 7:
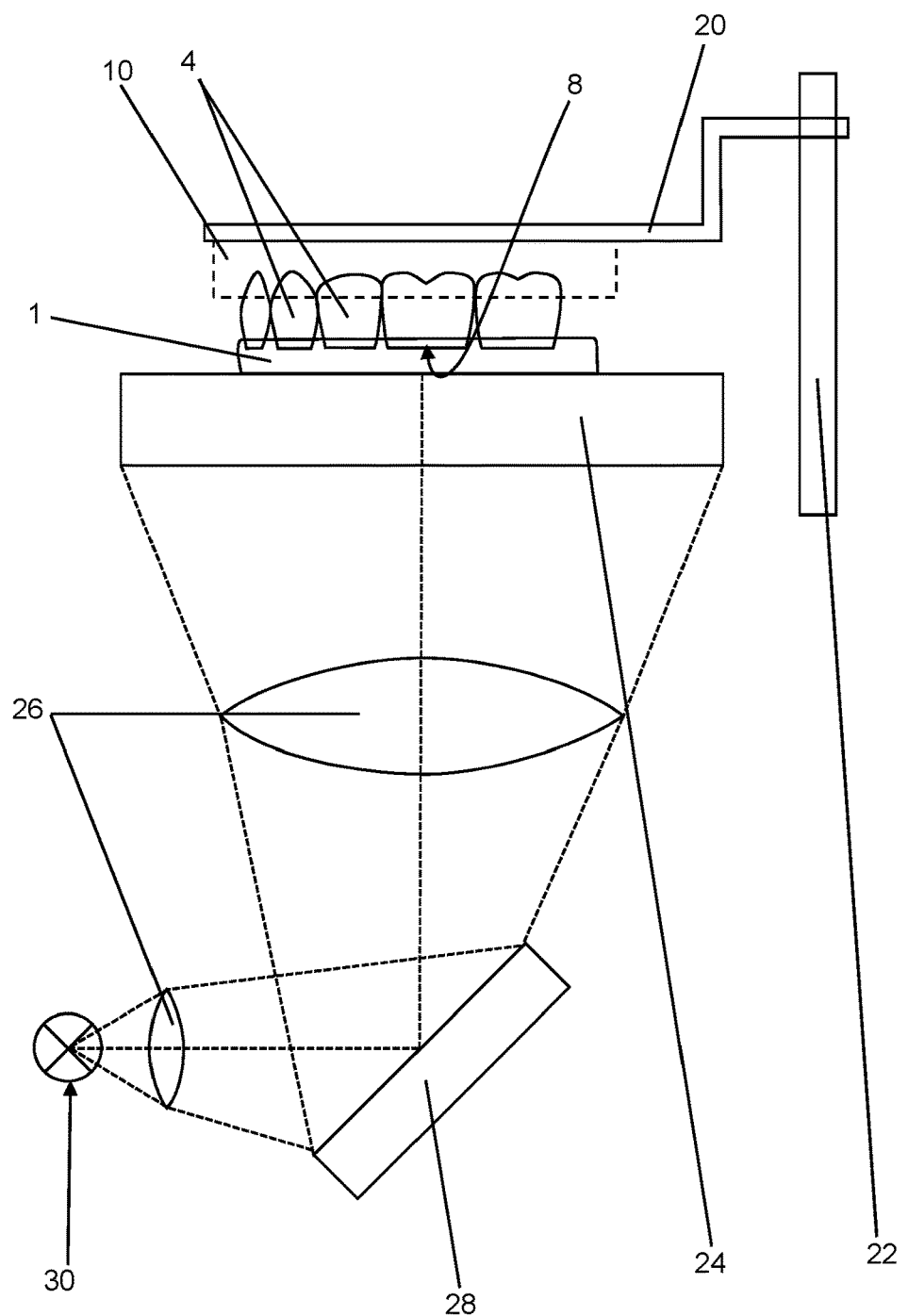
FIG. 7: the layered printing of the prosthetic base onto the milled prosthetic teeth with a 3D printer, making use of a liquid resin which is curable under light.

This situation is shown in FIG. 7, in which it is shown that the prosthetic teeth 4 in the occlusion plate 10 are secured on a building platform 20 of a 3D printer. For this purpose the occlusion plate 10 can engage into a latch fitting (not shown) on the building platform 20, and latch in engagement with this. The building platform 20 can be moved with the aid of a drive motor 22, controlled by the 3D printer, in the direction of a Z-axis perpendicular to the occlusion plate 10

(in FIG. 7 from the top downwards). Arranged underneath the building platform 20 and the occlusion plate 10 with the prosthetic teeth 4, of which the basal sides 8 are all located in one plane, is a basin open upwards, with a liquid resin 24. The liquid resin 24 can be cured or hardened with the aid of light. The base of the resin basin is transparent, such that the liquid resin 24 can be illuminated from beneath. The occlusion plate 10 is represented as transparent in FIG. 7 by a rectangle formed with broken lines, in order to show clearly the position of the prosthetic teeth 4 in the occlusion plate 10. At the beginning of the printing process, the prosthetic teeth 4 are immersed with the basal side by some millimeters, up to some 20 millimeters, depending on the length of the prosthetic teeth 4, into the resin bath 24 or, respectively, into the liquid resin 24.

For a better connection of the prosthetic teeth 4 with the hardening liquid resin 24, the surfaces, in particular the basal surfaces 8 of the prosthetic teeth 4, can be prepared by roughing or swelling with a solvent agent. For this purpose the prosthetic teeth 4 are roughed on the basal side 8 (for example mechanically by sand-blasting or chemically with a suitable solvent) and/or swelled with a liquid containing methyl methacrylate (MMA). As an MMA-containing liquid, use can be made, for example, of Palabond® from Heraeus Kulzer GmbH.

The occlusion plate 10 with the prosthetic teeth 4 is latch-engaged into a holding element provided for this purpose on the building platform 20 of the 3D printer in a clearly defined position. Next, based on the CAD model of the prosthetic base 1, the physical prosthetic base 1 is formed layer by layer.

For the layered forming onto the basally plane-levelled prosthetic teeth 4, the prosthetic base 1, contrary to the method with separate production of the prosthetic base 1, is preferably aligned with its longitudinal axis only parallel to the surface of the resin, as represented in FIG. 7.

Of the two orientation possibilities which derive from this:

1. Lowering of the arranged prosthetic teeth 4 or, respectively, the building platform 20 in the resin bath 24 and illuminating the resin layer from above, or
2. raising the arranged prosthetic teeth 4 or, respectively, the building platform 20 out of the resin bath 24 and illuminating from below through the base of the basin, the raising out of the resin bath 24 is favored (as represented in FIG. 7), since by this means, as appropriate, work can be carried out without the provision of additional support structures.

Further, with forming moving downwards, macromechanical retentions can be formed on the basal sides 8 of the prosthetic teeth 4, since with this arrangement the deposit of the new resin layer will not be smoothed by a wiper.

The illumination is provided by a system of lenses 26 and a micromirror array 28 and a light source 30. As the micromirror array 28, or, respectively, a Digital Micromirror Device (DMD), use can be made, for example, of a device for Digital Light Processing® (DLP) from Texas Instruments. Due to the illumination, the resin 24 on the basal sides 8 of the prosthetic teeth 4 is cured and hardened, and adheres there. The prosthetic base 1 is formed on this layer by layer, and, in the manner usual with known 3D printing processes, the prosthetic base 1 is printed on.

After the end of the printing process, the dental prosthesis can be taken out of the occlusion plate 10 and post-cured. The residues of the resin on the prosthesis surface are removed by cleaning in ethanol or isopropanol in the ultrasound bath. Polishing of the prosthetic base 1 smooths the surface, protects it against plaque deposits, and lends the dental prosthesis an aesthetic appearance.

The method according to the invention can be carried out with occlusion plates 10 which are produced manually or by means of Rapid Prototyping techniques. Likewise, the method can alternatively also be applied on pressed prosthetic teeth 4 or prosthetic teeth rows 4.

Figure 8:
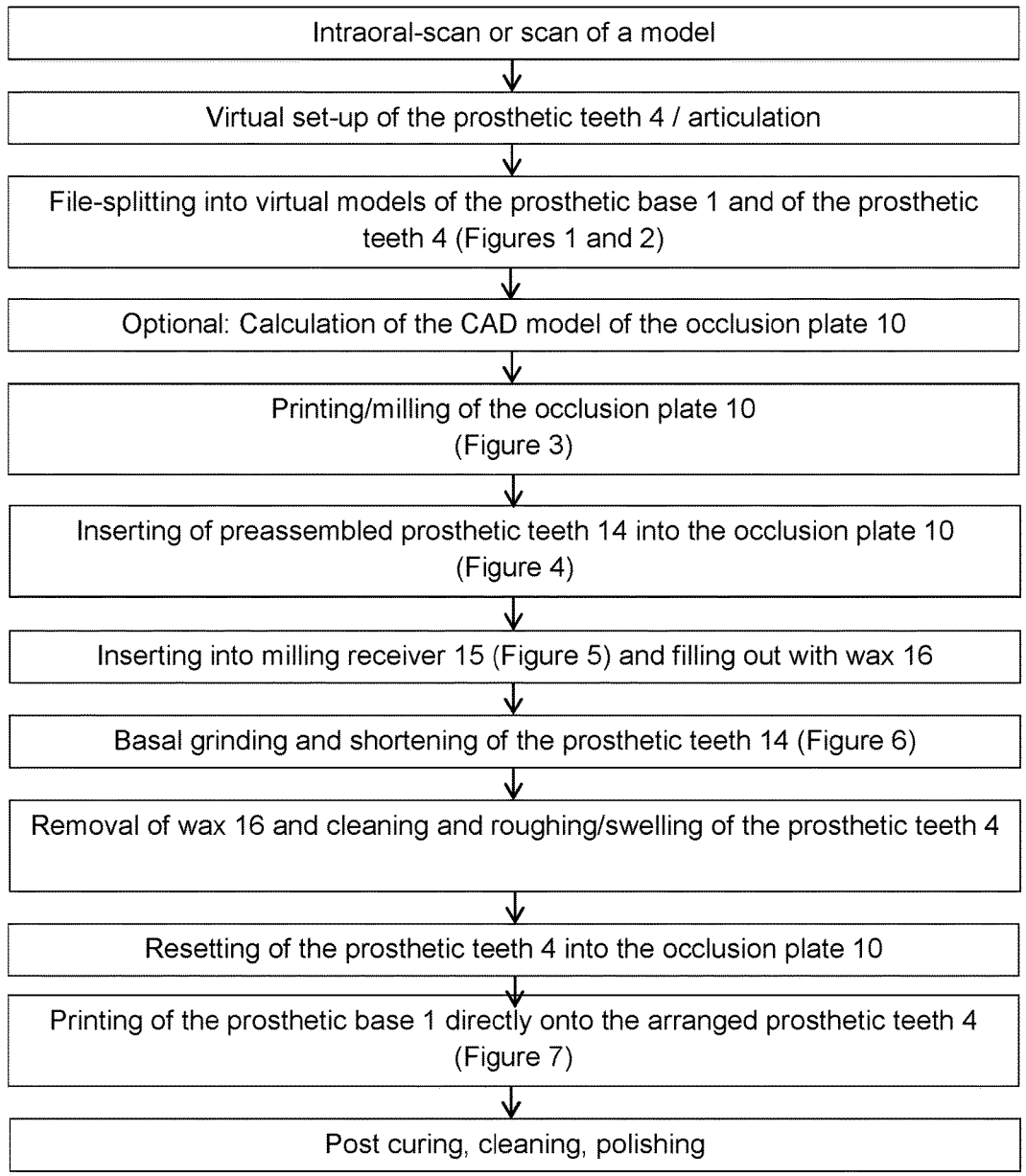
FIG. 8: an exemplary sequence diagram for a method according to the invention.

Shown in FIG. 8 is an exemplary sequence diagram for a method according to the invention.

The features of the invention disclosed in the foregoing description, as well as in the claims, figures, the sequence diagram, and the exemplary embodiments can be seen as essential individually as well as in any desired combination for the realization of the invention in its different embodiment forms.

REFERENCE FIGURE LIST

1 Prosthetic base
2 Surface for the fixing of prosthetic teeth
4 Prosthesis tooth/tooth row
6 Coronal surface/coronal side of the prosthesis tooth
8 Basal surface/basal side of the prosthesis tooth
10 Occlusion plate
12 Receiver surfaces for the coronal sides of the prosthetic teeth
14 Preassembled prosthesis tooth
15 Milling holding element
16 Wax
18 Milling machine
20 Building platform
22 Drive motor
24 Liquid resin/resin bath
26 Lens
28 Micromirror array
30 Light source

The invention claimed is:

1. Method for producing a dental prosthesis, wherein the dental prosthesis comprises a prosthetic base and a plurality of prosthetic teeth, wherein the method is carried out with the use of a virtual three-dimensional dental prosthesis model of the dental prosthesis which is to be produced, and wherein the virtual three-dimensional dental prosthesis model comprises virtual prosthetic teeth and a virtual prosthetic base, the method comprising the following consecutive steps:

A) producing a physical occlusion plate, wherein a region of a surface of the occlusion plate is formed by a negative of coronal sides of the virtual prosthetic teeth of the virtual dental prosthesis model, wherein location and orientation of the virtual prosthetic teeth relative to one another corresponding to the virtual dental prosthesis model are retained in a shape of the surface of the occlusion plate;

B) placing and securing preassembled prosthetic teeth on the occlusion plate, wherein coronal sides of the preassembled prosthetic teeth are placed on the surface of the occlusion plate formed by the negative;

C) securing the occlusion plate, with the prosthetic teeth secured therein, in a device for the layered forming of three-dimensional plastic structures; and D) printing the prosthetic base onto basal ends of the prosthetic teeth with the device for the layered forming of three-dimensional plastic structures on the basis of the shape of the virtual prosthetic base.

2. Method according to claim 1, comprising, after step B) and before step D), carrying out a basal ablation of the preassembled prosthetic teeth secured to the occlusion plate, wherein the prosthetic teeth are adjusted by the basal ablation to the shape of the virtual prosthetic teeth and/or of the virtual prosthetic base.

3. Method according to claim 2, comprising basally shortening the preassembled prosthetic teeth in such a way that basal surfaces of all the prosthetic teeth lie in one plane or essentially in one plane.

4. Method according to claim 3, comprising removing the basally shortened prosthetic teeth from the occlusion plate and freeing the basally shortened prosthetic teeth of any residues, and again securing the prosthetic teeth in the occlusion plate before step C).

5. Method according to claim 4, wherein the residues comprise retaining means for retaining the prosthetic teeth in the occlusion plate.

6. Method according to claim 5, wherein the retaining means comprise a wax or a milling wax.

7. Method according to claim 1, comprising, for producing the physical occlusion plate, calculating a virtual model of the occlusion plate from a position and an orientation of the coronal sides of the virtual prosthetic teeth of the virtual three-dimensional dental prosthesis model, to form a region of the virtual occlusion plate by a negative of the coronal sides of the virtual prosthetic teeth, wherein the position and orientation of the coronal sides of the virtual prosthetic teeth relative to one another corresponding to the dental prosthesis model are retained in the negative, and the producing the physical occlusion plate by a CAM process on the basis of data of the virtual model of the occlusion plate.

8. Method according to claim 1, comprising, before step C), basally roughening the prosthetic teeth in at least some regions and/or swelling the prosthetic teeth in at least some regions with a solvent.

9. Method according to claim 8, comprising, before step C), basally roughening the prosthetic teeth in at least some regions and/or swelling the prosthetic teeth in at least some regions with a solvent after cleaning the prosthetic teeth and after re-securing the prosthetic teeth in the occlusion plate.

10. Method according to claim 1, comprising, in step C), securing the occlusion plate in a clearly defined position in a holding element on a structuring platform of the device for the layered forming of three-dimensional plastic structures.

11. Method according to claim 10, comprising, in step C), latch-fitting the occlusion plate in a clearly defined position in a holding element on a structuring platform of the device for the layered forming of three-dimensional plastic structures.

12. Method according to claim 1, comprising printing the prosthetic base onto the prosthetic teeth in layers.

13. Method according to claim 12, comprising applying the printed-on layers of the prosthetic base in a plane parallel to the occlusion plane or parallel to the transversal plane of the denture which is to be produced.

14. Method according to claim 12, comprising carrying out the printing by curing a liquid curable resin on a resin surface of a resin bath, wherein the basal ends of the prosthetic teeth are laid on or at the resin surface and/or the basal ends of the prosthetic teeth are immersed into the resin bath.

15. Method according to claim 14, comprising forming the layers by sinking the prosthetic teeth in the resin bath, applying an illumination of the liquid resin for the purpose of curing from above the resin surface, or raising the prosthetic teeth out of the resin bath, and performing an illumination of the liquid resin for the purpose of curing from below the resin surface.

16. Method according to claim 1, comprising, after step D), removing the dental prosthesis comprising the printed-on prosthetic base and the prosthetic teeth secured therein from the occlusion plate, and then cleaning the dental prosthesis, post-curing the dental prosthesis, and/or polishing the prosthetic base.

17. Method according to claim 1, comprising computationally dividing the virtual three-dimensional dental prosthesis model by file-splitting into a three-dimensional model of the virtual prosthetic teeth and a virtual three-dimensional model of the prosthetic base.

18. Method according to claim 1, comprising producing the virtual three-dimensional dental prosthesis model on the basis of an intraoral scan for shaping the virtual prosthetic base and by virtually setting virtual models of the preassembled prosthetic teeth in the virtual prosthetic base.

19. Method according to claim 18, comprising selecting the shape, the location, and/or the orientation of the prosthetic teeth by simulating the position of the dental prosthesis in an oral cavity of a patient.

20. Method according to claim 19, comprising selecting the shape, the location, and/or the orientation of the prosthetic teeth by simulating an occlusion plane and/or chewing movements of the oral cavity.

21. Method according to claim 1, comprising basally ablating the preassembled prosthetic teeth on the basis of the virtual model of the prosthetic teeth with a CAM method, such that the basal shape of the preassembled prosthetic teeth is adjusted to the virtual prosthetic base in such a way that an outer shape of the prosthetic base with the prosthetic teeth fitted corresponds to an outer shape of the virtual dental prosthesis model.

22. Method according to claim 21, comprising basally ablating the preassembled prosthetic teeth on the basis of the virtual model of the prosthetic teeth with a CAM method by milling.

23. Method according to any claim 1, comprising using data relating to the outer shape of known preassembled prosthetic teeth for calculating the virtual dental prosthesis model.

24. Method according to claim 1, comprising fixing the preassembled prosthetic teeth fitted to the occlusion plate with the aid of a fluid fixing means which is to be hardened in a holding element, and then fixing the holding element in the device for the layered forming of three-dimensional plastic structures or in a computer-controlled milling device to print on the prosthetic base, and then basally ablating or roughening the prosthetic teeth.

25. Method according to claim 1, comprising printing the prosthetic base onto the basal ends of the prosthetic teeth layer by layer, wherein a thickness of the layers is always the same thickness and/or a thickness of the printed-on plastic structure measures for each layer is 1 µm to 500 µm.

26. Method according to claim 25, comprising printing the prosthetic base onto the basal ends of the prosthetic teeth layer by layer, wherein a thickness of the layers is always the same thickness and/or a thickness of the printed-on plastic structure measures for each layer is 10 µm to 200 µm.

27. Method according to claim 26, comprising printing the prosthetic base onto the basal ends of the prosthetic teeth layer by layer, wherein a thickness of the layers is always the same thickness and/or a thickness of the printed-on plastic structure measures for each layer is 25 µm to 100 µm.

28. Dental prosthesis produced with a method according to claim 1.

29. Device or combination of devices for carrying out a method according to claim 1, comprising a device for layered forming of three-dimensional plastic structures and a computer for calculating the virtual model and to control a CAM device.

30. Device or combination of devices for carrying out a method according to claim 29, additionally comprising a computer-controlled milling device.

31. Occlusion plate produced by a CAD/CAM process for implementing a method according to claim 1.

* * * * *